(12) United States Patent
Wu et al.

(10) Patent No.: US 7,517,495 B2
(45) Date of Patent: Apr. 14, 2009

(54) BIOLOGICAL SPECIMEN COLLECTION AND ANALYSIS SYSTEM

(75) Inventors: Yuzhang Wu, Zhejiang (CN); Ying Yang, Zhejiang (CN); Jieling Dai, Zhejiang (CN); Hsiaoho Edward Tung, San Diego, CA (US)

(73) Assignee: Inverness Medical Switzerland GmbH (CH)

( * ) Notice: Subject to any disclaimer, the term of this patent is extended or adjusted under 35 U.S.C. 154(b) by 640 days.

(21) Appl. No.: 10/766,204

(22) Filed: Jan. 27, 2004

(65) Prior Publication Data

US 2005/0048670 A1 Mar. 3, 2005

Related U.S. Application Data

(60) Provisional application No. 60/497,853, filed on Aug. 25, 2003.

(51) Int. Cl.
*G01N 33/00* (2006.01)

(52) U.S. Cl. .......................... 422/61; 422/68.1; 422/99; 422/102; 422/104

(58) Field of Classification Search .................. 422/61, 422/50, 55, 58, 68.1, 99, 100, 102, 104
See application file for complete search history.

(56) References Cited

U.S. PATENT DOCUMENTS

| | | | |
|---|---|---|---|
| 228,031 | A | 5/1880 | Broughton et al. |
| 424,982 | A | 4/1890 | Hidden |

(Continued)

FOREIGN PATENT DOCUMENTS

EP  0 250 137  6/1987

(Continued)

OTHER PUBLICATIONS

U.S. Appl. No. 10/717,082, filed Nov. 19, 2003.

(Continued)

*Primary Examiner*—Sam P Siefke
(74) *Attorney, Agent, or Firm*—Wilson Sonsini Goodrich & Rosati

(57) ABSTRACT

Disclosed is a device for collecting a fluid specimen. The device comprises a container that can receive a fluid specimen; a plunger movably positioned within the container, wherein the plunger can move from an initial position at an upper region of the container to a secondary position below the first position; a fluid segregation chamber that can receive a portion of the fluid specimen from the container, wherein any fluid in the segregation chamber is segregated from the fluid specimen in the container; a fluid flow lumen that provides a passageway for at least a portion of the fluid specimen to flow into the fluid segregation chamber, wherein a first end of the passageway has a first opening that opens into the fluid segregation chamber and a second end of the passageway has a second opening that can receive at least a portion of the fluid specimen; and a seal member that covers the first opening or the second opening to prevent fluid from flowing therethrough. A test element can be used to push the plunger from the initial position toward the secondary position to break the seal member and cause at least a portion of the fluid specimen to flow through the second opening into the fluid flow lumen and into the fluid segregation chamber through the first opening.

25 Claims, 9 Drawing Sheets

U.S. PATENT DOCUMENTS

| | | | | |
|---|---|---|---|---|
| 645,430 A | 3/1900 | Smelker et al. | | |
| 711,452 A | 10/1902 | Meyer et al. | | |
| D140,925 S | 4/1945 | Christner et al. | ............. | D3/203 |
| 3,000,540 A | 9/1961 | Wheeler | ...................... | 222/14 |
| 3,658,216 A | 4/1972 | Schwartzman | ............... | 222/453 |
| 3,687,333 A | 8/1972 | Burnett et al. | ................. | 220/46 |
| 3,688,942 A | 9/1972 | Michell et al. | ................. | 220/46 |
| 3,723,064 A | 3/1973 | Liotta | ......................... | 23/230 |
| 3,837,518 A | 9/1974 | Gach | ............................ | 215/7 |
| 3,951,748 A | 4/1976 | Devlin | ..................... | 195/103.5 |
| 3,990,850 A | 11/1976 | Friedman et al. | .......... | 435/287.9 |
| 4,024,976 A | 5/1977 | Acton | ......................... | 215/32 |
| 4,063,460 A | 12/1977 | Svensson | .................... | 73/425.6 |
| 4,087,326 A | 5/1978 | Kereluk | .................... | 195/103.5 |
| 4,087,332 A | 5/1978 | Hansen | ...................... | 195/127 |
| 4,111,329 A | 9/1978 | Lampman | ................... | 220/266 |
| D250,129 S | 10/1978 | Skinner | ..................... | D24/121 |
| 4,133,639 A | 1/1979 | Harte | ............................ | 23/230 |
| 4,165,018 A | 8/1979 | Giggard | ...................... | 220/284 |
| 4,177,930 A | 12/1979 | Crisci | .......................... | 220/284 |
| 4,190,175 A | 2/1980 | Allen | ............................ | 220/270 |
| 4,205,043 A | 5/1980 | Esch et al. | ................... | 422/72 |
| 4,211,749 A | 7/1980 | Kantner | ...................... | 422/102 |
| 4,237,234 A | 12/1980 | Meunier | ..................... | 435/301 |
| D258,311 S | 2/1981 | Peterson | .................... | D24/121 |
| 4,270,921 A | 6/1981 | Graas | .......................... | 23/230 B |
| 4,275,149 A | 6/1981 | Litman et al. | .................... | 435/7 |
| 4,298,345 A | 11/1981 | Sodickson et al. | ........ | 23/230 R |
| 4,299,916 A | 11/1981 | Litman et al. | .................... | 435/6 |
| 4,301,139 A | 11/1981 | Feingers et al. | ................ | 424/1 |
| 4,313,734 A | 2/1982 | Leuvering | ................. | 23/230 B |
| 4,323,536 A | 4/1982 | Columbus | .................... | 422/56 |
| 4,338,094 A | 7/1982 | Elahi | ......................... | 23/230 B |
| 4,361,537 A | 11/1982 | Deutsch et al. | ............... | 422/56 |
| 4,376,110 A | 3/1983 | David et al. | ................. | 436/513 |
| 4,391,904 A | 7/1983 | Litman et al. | .................... | 435/7 |
| 4,394,944 A | 7/1983 | Rech | .......................... | 222/553 |
| 4,421,244 A | 12/1983 | Van Melle | .................. | 220/306 |
| 4,425,438 A | 1/1984 | Bauman et al. | ............. | 436/527 |
| 4,426,451 A | 1/1984 | Columbus | ................... | 436/518 |
| 4,435,504 A | 3/1984 | Zuk et al. | ....................... | 435/7 |
| 4,446,232 A | 5/1984 | Liotta | ............................ | 435/7 |
| 4,462,510 A | 7/1984 | Steer et al. | ................... | 222/48 |
| 4,474,892 A | 10/1984 | Murad et al. | ................. | 436/513 |
| 4,476,993 A | 10/1984 | Krout | .......................... | 220/276 |
| 4,485,938 A | 12/1984 | Williams | .................... | 221/154 |
| 4,493,432 A | 1/1985 | Smith | .......................... | 220/270 |
| 4,512,493 A | 4/1985 | Von Holdt | ................... | 220/306 |
| 4,517,288 A | 5/1985 | Giegel et al. | .................... | 435/7 |
| 4,535,057 A | 8/1985 | Dreesman et al. | ............... | 435/5 |
| 4,646,926 A | 3/1987 | Agbay et al. | ................. | 215/203 |
| 4,659,678 A | 4/1987 | Forrest et al. | ............. | 436/512 |
| 4,666,863 A | 5/1987 | Edwards et al. | ............. | 436/514 |
| D290,136 S | 6/1987 | Ball et al. | ...................... | D24/9 |
| 4,673,657 A | 6/1987 | Christian | .................... | 436/501 |
| 4,678,757 A | 7/1987 | Rapkin et al. | ................. | 436/169 |
| 4,700,860 A | 10/1987 | Li | ................................ | 215/256 |
| 4,711,364 A | 12/1987 | Letica | ......................... | 220/276 |
| 4,718,571 A | 1/1988 | Bordner | ...................... | 220/270 |
| 4,722,458 A | 2/1988 | Van Dal | ...................... | 222/105 |
| 4,725,406 A | 2/1988 | Compton et al. | ............... | 422/58 |
| 4,740,468 A | 4/1988 | Weng et al. | ..................... | 435/7 |
| 4,752,448 A | 6/1988 | Wells et al. | ................. | 422/56 |
| 4,769,215 A | 9/1988 | Ehrenkranz | ................... | 422/58 |
| 4,366,241 A | 10/1988 | Tom et al. | ..................... | 435/7 |
| D299,744 S | 2/1989 | Bauer | ......................... | D24/17 |
| 4,806,311 A | 2/1989 | Greenquist | ................... | 422/56 |
| 4,806,487 A | 2/1989 | Akers et al. | ................... | 436/93 |
| 4,807,771 A | 2/1989 | Roy et al. | .................... | 215/252 |
| 4,837,168 A | 6/1989 | de Jaeger et al. | ............. | 436/533 |
| 4,853,335 A | 8/1989 | Olsen et al. | ................. | 436/527 |
| 4,855,240 A | 8/1989 | Rosenstein et al. | .......... | 436/514 |
| 4,857,453 A | 8/1989 | Ullman et al. | ................. | 435/7 |
| 4,886,184 A | 12/1989 | Chamourian | ................ | 220/306 |
| 4,900,663 A | 2/1990 | Wie et al. | ....................... | 435/7 |
| 4,923,680 A | 5/1990 | Nelson | ......................... | 422/58 |
| 4,938,927 A | 7/1990 | Kelton et al. | ................... | 422/64 |
| 4,943,522 A | 7/1990 | Eisinger et al. | ................. | 435/7 |
| 4,952,517 A | 8/1990 | Bahar | .......................... | 436/518 |
| 4,954,452 A | 9/1990 | Yost et al. | ..................... | 436/524 |
| 4,959,324 A | 9/1990 | Ramel et al. | ................. | 436/169 |
| 4,960,691 A | 10/1990 | Gordon et al. | ................. | 435/6 |
| 4,961,351 A | 10/1990 | Gerken | ..................... | 73/864.65 |
| 4,966,302 A | 10/1990 | Hjordie | ...................... | 220/306 |
| 4,973,549 A | 11/1990 | Khanna et al. | ................. | 435/11 |
| 4,981,786 A | 1/1991 | Dafforn et al. | ................. | 435/7 |
| 4,987,085 A | 1/1991 | Allen et al. | ................... | 436/169 |
| 5,002,198 A | 3/1991 | Smith | ......................... | 220/276 |
| 5,006,474 A | 4/1991 | Horstman et al. | ............ | 436/524 |
| 5,028,535 A | 7/1991 | Buechler et al. | ............. | 435/7.1 |
| 5,069,878 A | 12/1991 | Ehrenkranz | .................. | 422/61 |
| 5,073,484 A | 12/1991 | Swanson et al. | ............ | 435/7.92 |
| 5,075,078 A | 12/1991 | Osikowicz et al. | ............ | 422/56 |
| 5,079,142 A | 1/1992 | Coleman et al. | ............. | 435/7.92 |
| 5,082,626 A | 1/1992 | Grage, Jr. | ..................... | 422/56 |
| 5,085,988 A | 2/1992 | Olson | ......................... | 435/7.91 |
| 5,089,391 A | 2/1992 | Buechler et al. | ............. | 435/7.1 |
| 5,092,478 A | 3/1992 | La Pierre | .................... | 215/256 |
| 5,096,837 A | 3/1992 | Fan et al. | ..................... | 436/514 |
| 5,111,947 A | 5/1992 | Patterson | .................... | 215/256 |
| 5,115,934 A | 5/1992 | Nelson | ........................ | 220/276 |
| 5,116,576 A | 5/1992 | Stanley | ........................ | 422/55 |
| 5,118,607 A | 6/1992 | Bignami et al. | ............. | 435/7.1 |
| 5,119,830 A | 6/1992 | Davis | ......................... | 600/584 |
| 5,120,643 A | 6/1992 | Ching et al. | ................ | 435/7.92 |
| 5,135,199 A | 8/1992 | Cross et al. | .................. | 251/319 |
| 5,141,850 A | 8/1992 | Cole et al. | ................... | 436/525 |
| 5,141,875 A | 8/1992 | Kelton et al. | ................. | 436/514 |
| 5,156,952 A | 10/1992 | Litman et al. | .............. | 435/7.91 |
| 5,165,572 A | 11/1992 | Bath | ............................ | 222/83.5 |
| 5,185,127 A | 2/1993 | Vonk | ........................... | 422/56 |
| 5,186,367 A | 2/1993 | Hickerson | ................... | 222/207 |
| 5,186,897 A | 2/1993 | Eason et al. | .................. | 422/100 |
| 5,202,268 A | 4/1993 | Kuhn et al. | ................. | 436/525 |
| 5,207,340 A | 5/1993 | Cochrane | .................... | 215/256 |
| 5,232,835 A | 8/1993 | Litman et al. | ............. | 435/7.93 |
| 5,238,652 A | 8/1993 | Sun et al. | ........................ | 422/61 |
| RE34,394 E | 9/1993 | Bunting | ........................ | 436/500 |
| 5,252,496 A | 10/1993 | Kang et al. | .................. | 436/529 |
| D341,663 S | 11/1993 | Coulter | ....................... | D24/225 |
| 5,260,193 A | 11/1993 | Olson | ........................ | 435/7.91 |
| 5,266,497 A | 11/1993 | Imai et al. | .................... | 436/514 |
| 5,270,166 A | 12/1993 | Parsons et al. | ............... | 435/7.4 |
| 5,271,517 A | 12/1993 | Bowers | ....................... | 220/276 |
| 5,275,785 A | 1/1994 | May et al. | ..................... | 422/56 |
| 5,279,330 A | 1/1994 | Debush | ........................ | 137/853 |
| 5,294,015 A | 3/1994 | Landis | ........................ | 220/306 |
| 5,296,347 A | 3/1994 | LaMotte, III | .................. | 435/5 |
| 5,308,775 A | 5/1994 | Donovan et al. | ............. | 436/518 |
| 5,312,009 A | 5/1994 | Ratajczak et al. | ........... | 220/258 |
| 5,354,692 A | 10/1994 | Yang et al. | ................... | 436/514 |
| 5,356,782 A | 10/1994 | Moorman et al. | ............. | 435/7.9 |
| 5,381,918 A | 1/1995 | Dahl | ............................ | 220/256 |
| 5,395,754 A | 3/1995 | Lambotte et al. | .......... | 435/607.4 |
| 5,399,486 A | 3/1995 | Cathey et al. | ................ | 435/7.9 |
| 5,403,551 A | 4/1995 | Galloway et al. | ............ | 422/58 |
| 5,415,994 A | 5/1995 | Imrich et al. | ................... | 435/5 |
| 5,416,000 A | 5/1995 | Allen et al. | ................ | 435/7.92 |
| 5,424,193 A | 6/1995 | Pronovost et al. | ........... | 435/7.32 |
| 5,429,804 A | 7/1995 | Sayles | ......................... | 422/58 |
| 5,435,970 A | 7/1995 | Mamenta et al. | .............. | 422/56 |
| D361,842 S | 8/1995 | Nazareth et al. | .............. | D24/225 |
| 5,451,504 A | 9/1995 | Fitzpatrick et al. | ............. | 435/7.2 |
| D366,938 S | 2/1996 | Shartle et al. | .............. | D24/224 |

| | | | | | | |
|---|---|---|---|---|---|---|
| 5,489,414 | A | 2/1996 | Schreiber et al. ............... 422/64 | 6,382,444 B1 | 5/2002 | Nyman ........................ 215/252 |
| 5,500,350 | A | 3/1996 | Baker et al. ................. 435/7.92 | 6,403,383 B1 | 6/2002 | Casterlin et al. ............ 436/518 |
| D369,868 | S | 5/1996 | Nazareth et al. ........... D24/225 | 6,406,922 B2 | 6/2002 | Casterlin et al. ............ 436/518 |
| 5,523,051 | A | 6/1996 | Gibson .......................... 422/1 | D464,141 S | 10/2002 | McMenamy et al. ........ D24/216 |
| 5,523,055 | A | 6/1996 | Hansen et al. ................. 422/58 | 6,464,939 B1 | 10/2002 | Bachand et al. ................. 422/58 |
| 5,591,645 | A | 1/1997 | Rosenstein .................. 436/514 | 6,468,474 B2 | 10/2002 | Bachand et al. ................. 422/58 |
| 5,595,187 | A | 1/1997 | Davis ......................... 128/771 | D468,204 S | 1/2003 | Gittens et al. ................ D9/430 |
| 5,597,532 | A | 1/1997 | Connolly ..................... 422/58 | D468,437 S | 1/2003 | McMenamy et al. ........ D24/216 |
| 5,601,191 | A | 2/1997 | Meador ...................... 206/569 | 6,565,808 B2 | 5/2003 | Hudak et al. ................... 422/58 |
| 5,602,040 | A | 2/1997 | May et al. .................. 436/514 | 6,576,193 B1 | 6/2003 | Cui et al. ...................... 422/58 |
| 5,622,871 | A | 4/1997 | May et al. .................. 436/514 | 6,669,908 B2 | 12/2003 | Weyker et al. ................. 422/58 |
| 5,641,012 | A | 6/1997 | Silversides .................. 141/383 | 6,759,190 B2 | 7/2004 | Lin et al. ........................ 435/4 |
| 5,641,637 | A | 6/1997 | Hudak et al. ............... 435/7.24 | 6,890,484 B2 | 5/2005 | Bautista et al. ................. 422/58 |
| 5,654,162 | A | 8/1997 | Guire et al. ................. 435/7.92 | 2002/0004019 A1 | 1/2002 | Bachand et al. ................. 422/58 |
| 5,656,503 | A | 8/1997 | May et al. .................. 436/514 | 2002/0023482 A1 | 2/2002 | Pampinella .................. 73/49.8 |
| D384,971 | S | 10/1997 | Kawan .......................... D19/9 | 2002/0031845 A1 | 3/2002 | Cipkowski ................... 436/518 |
| D388,167 | S | 12/1997 | Caradonna et al. ......... D24/107 | 2002/0046614 A1 | 4/2002 | Alley ....................... 73/864.91 |
| 5,712,172 | A | 1/1998 | Huang et al. ................ 436/518 | 2002/0058031 A1 | 5/2002 | Tung et al. ................. 424/140.1 |
| D390,667 | S | 2/1998 | Nazareth .................... D24/223 | 2002/0085953 A1 | 7/2002 | Parker ......................... 422/61 |
| 5,714,389 | A | 2/1998 | Charlton et al. ............. 436/514 | 2002/0137231 A1 | 9/2002 | Cipkowski ................... 436/518 |
| 5,716,778 | A | 2/1998 | Weng et al. ..................... 435/4 | 2002/0173047 A1 | 11/2002 | Hudak et al. ................. 436/178 |
| 5,728,587 | A | 3/1998 | Kang et al. .................. 436/518 | 2003/0004396 A1 | 1/2003 | Vanden Hock et al. ......... 600/37 |
| 5,739,041 | A | 4/1998 | Nazareth et al. ............. 436/518 | 2003/0021727 A1 | 1/2003 | Weyker et al. ................. 422/58 |
| D395,708 | S | 6/1998 | Shartle et al. .............. D24/224 | 2003/0021736 A1 | 1/2003 | Kang et al. |
| 5,770,460 | A | 6/1998 | Pawlak et al. ............... 436/510 | 2003/0022392 A1 | 1/2003 | Hudak ........................ 436/518 |
| 5,785,044 | A | 7/1998 | Meador et al. .............. 128/760 | 2003/0027359 A1 | 2/2003 | Hudak et al. ................ 436/518 |
| 5,807,752 | A | 9/1998 | Brizgys et al. ............... 436/513 | 2003/0036742 A1 | 2/2003 | Carano et al. ................ 604/409 |
| 5,843,691 | A | 12/1998 | Douglas et al. ................ 435/14 | 2003/0053938 A1 | 3/2003 | Szeles ........................ 422/102 |
| 5,846,835 | A | 12/1998 | Sisbarro et al. .............. 436/166 | 2003/0129767 A1 | 7/2003 | Lorraine et al. ............. 436/178 |
| D404,812 | S | 1/1999 | Cipkowski ................. D24/107 | 2004/0132091 A1 | 7/2004 | Ramsey et al. ............... 435/7.1 |
| 5,869,006 | A | 2/1999 | Fanning et al. ................ 422/67 | 2004/0133128 A1 | 7/2004 | Guan et al. .................. 600/584 |
| 5,874,216 | A | 2/1999 | Mapes ............................ 435/6 | 2004/0136877 A1 | 7/2004 | Kang et al. .................. 422/100 |
| 5,877,028 | A | 3/1999 | Chandler et al. ............. 436/514 | 2004/0184954 A1 | 9/2004 | Guo et al. .................... 422/56 |
| 5,897,840 | A | 4/1999 | Owens, Jr. et al. ........... 422/102 | 2005/0106753 A1 | 5/2005 | Wu et al. .................... 436/180 |
| 5,904,898 | A | 5/1999 | Markart ....................... 422/61 | | | |
| 5,916,815 | A | 6/1999 | Lappe .......................... 422/56 | | | |
| 5,922,533 | A | 7/1999 | Vallari et al. ..................... 435/5 | | | |
| 5,922,615 | A | 7/1999 | Nowakowski et al. ....... 436/518 | | | |
| 5,929,422 | A | 7/1999 | Lappe ..................... 235/462.13 | | | |
| 5,932,430 | A | 8/1999 | Larka et al. ................. 435/7.32 | | | |
| 5,939,252 | A | 8/1999 | Lennon et al. ................... 435/4 | | | |
| 5,939,272 | A | 8/1999 | Buechler et al. ............. 435/7.1 | | | |
| 5,939,331 | A | 8/1999 | Burd et al. ................... 436/518 | | | |
| 5,962,333 | A | 10/1999 | Incorvia et al. .............. 436/169 | | | |
| 5,965,458 | A | 10/1999 | Kouvonen et al. ........... 436/518 | | | |
| 5,975,373 | A | 11/1999 | Forsberg ..................... 222/209 | | | |
| 5,976,469 | A | 11/1999 | Davis ......................... 422/102 | | | |
| 5,976,895 | A | 11/1999 | Cipkowski ................... 422/102 | | | |
| 5,981,293 | A | 11/1999 | Charlton ..................... 436/177 | | | |
| 5,989,921 | A | 11/1999 | Charlton et al. ............. 436/501 | | | |
| 5,994,145 | A | 11/1999 | Stave et al. .................. 436/139 | | | |
| D420,141 | S | 2/2000 | Casterlin ................... D24/223 | | | |
| 6,020,147 | A | 2/2000 | Guire et al. ................. 435/7.92 | | | |
| 6,025,203 | A | 2/2000 | Vetter et al. ................. 436/170 | | | |
| 6,087,184 | A | 7/2000 | Magginetti et al. .......... 436/514 | | | |
| D430,303 | S | 8/2000 | Cipkowski ................. D24/225 | | | |
| 6,096,563 | A | 8/2000 | Hajizadeh et al. ............ 436/523 | | | |
| D434,494 | S | 11/2000 | Wilkinson et al. .......... D24/122 | | | |
| 6,165,416 | A | 12/2000 | Chandler ..................... 422/58 | | | |
| 6,168,758 | B1 | 1/2001 | Forsberg et al. ................ 422/61 | | | |
| 6,170,719 | B1 | 1/2001 | Wilkinson et al. ........... 222/479 | | | |
| 6,171,261 | B1 | 1/2001 | Niermann et al. ........... 600/573 | | | |
| 6,174,006 | B1 | 1/2001 | Burt ............................ 292/307 | | | |
| 6,210,909 | B1 | 4/2001 | Guirguis ...................... 435/7.2 | | | |
| 6,248,598 | B1 | 6/2001 | Bogema ...................... 436/518 | | | |
| 6,277,646 | B1* | 8/2001 | Guirguis et al. ............. 436/165 | | | |
| D449,524 | S | 10/2001 | Kieras ........................ D9/430 | | | |
| 6,308,848 | B1 | 10/2001 | Parrinello ................... 215/252 | | | |
| 4,703,017 | C1 | 12/2001 | Campbell et al. ............ 436/501 | | | |
| 6,342,183 | B1* | 1/2002 | Lappe et al. .................. 422/58 | | | |
| 6,372,515 | B1 | 4/2002 | Casterlin et al. ............ 436/518 | | | |
| 6,375,897 | B1 | 4/2002 | Bachand ...................... 422/58 | | | |
| 6,379,620 | B1 | 4/2002 | Tydings et al. ................ 422/58 | | | |

FOREIGN PATENT DOCUMENTS

| | | |
|---|---|---|
| EP | 0 289 761 | 11/1988 |
| EP | 0 183 442 | 3/1990 |
| EP | 0 291 194 | 2/1994 |
| EP | 0 284 232 | 10/2002 |
| WO | 97/33519 | 9/1997 |
| WO | 98/38917 | 9/1998 |
| WO | 00/29111 | 5/2000 |
| WO | 00/62930 | 10/2000 |
| WO | 02/095396 | 11/2002 |
| WO | WO 03/106968 | 6/2003 |
| WO | WO 2004/038364 | 9/2003 |
| WO | 03/106968 | 12/2003 |
| WO | 2004/038364 | 5/2004 |
| WO | PCT/US2004/022524 | 7/2004 |
| WO | PCT/US2004/022525 | 7/2004 |
| WO | PCT/US2004/022528 | 7/2004 |
| WO | PCT/US2004/031635 | 9/2004 |
| WO | 2005/006959 | 1/2005 |
| WO | 2005/007067 | 1/2005 |
| WO | 2005/008216 | 1/2005 |
| WO | 2005/023426 | 3/2005 |
| WO | 2005/031351 | 4/2005 |
| WO | 2005/050165 | 6/2005 |
| WO | 2005/050166 | 6/2005 |
| WO | 2005/050167 | 6/2005 |
| WO | 2005/050168 | 6/2005 |
| WO | 2005/050169 | 6/2005 |

OTHER PUBLICATIONS

"Status Cup Plus, Drug Screening System," LifeSign Brochure, pp. 1-2, no dated.
U.S. Appl. No. 09/915,494, filed Jul. 25, 2001.
U.S. Appl. No. 10/211,199, filed Aug. 2, 2002.
U.S. Appl. No. 09/579,673, filed May 26, 2000.
U.S. Appl. No. 10/336,204, filed Jan. 4, 2003.
U.S. Appl. No. 10/336,203, filed Jan. 4, 2003.

ACON Magazine Advertisement, *IVD Technology Magazine*, p. 17 Mar./Apr. 2000.

ACON Magazine Advertisement, *IVD Technology Magazine*, p. 45 Nov./Dec. 1999.

ACON Magazine Advertisement, *LabMedica Magazine*, p. 14 Jul./Aug. 1999; p. 9 Sep./Oct. 1999; p. 23 Nov./Dec. 1999.

ACON OEM Product Brochure, Aug. 2000.

ACON Product Brochure, "Is he using drugs?", (2003).

Drug Detection Devices, Ltd. www.3dl.net/drugtests.html, no date.

InTec Products, Inc. Product Brochure, "One step drug-of-abuse test", (2002).

Handbook: Urine Specimen Collection Handbook for Federal Workplace Drug Testing Programs, Health and Human Services (HHS) Mandatory Guidelines, *The National Clearinghouse for Alcohol and Drug Information*. www.health.org/workplace/urinebook.htm, no date.

\* cited by examiner

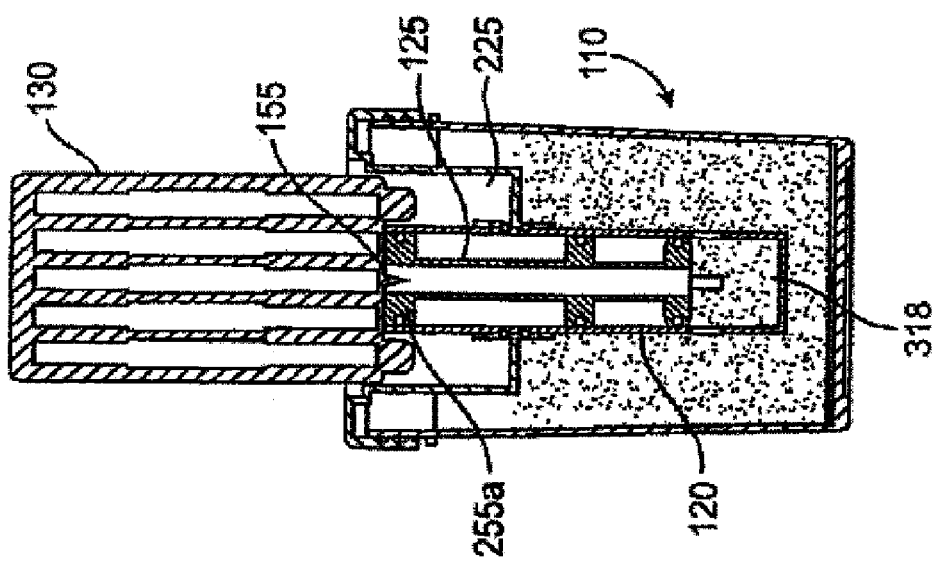
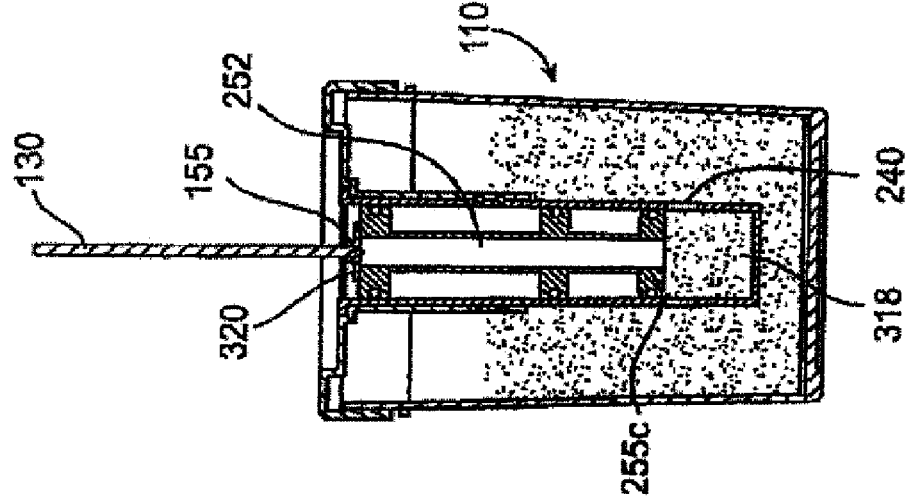
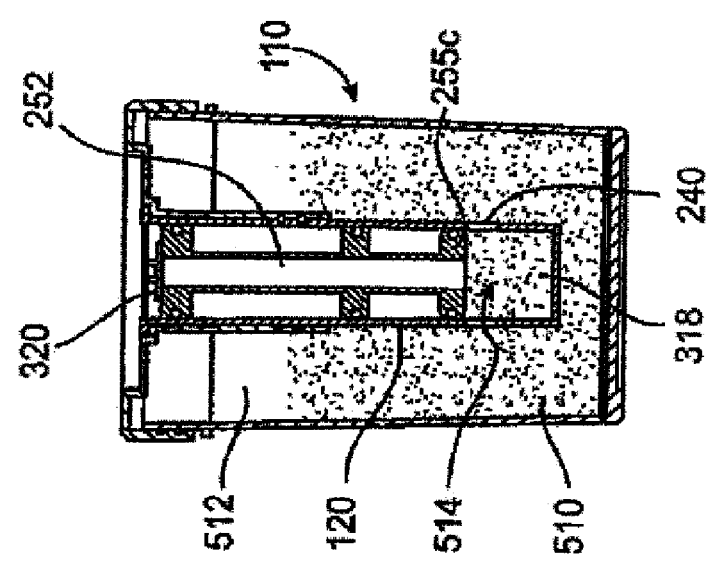
Fig. 5
Fig. 6
Fig. 7

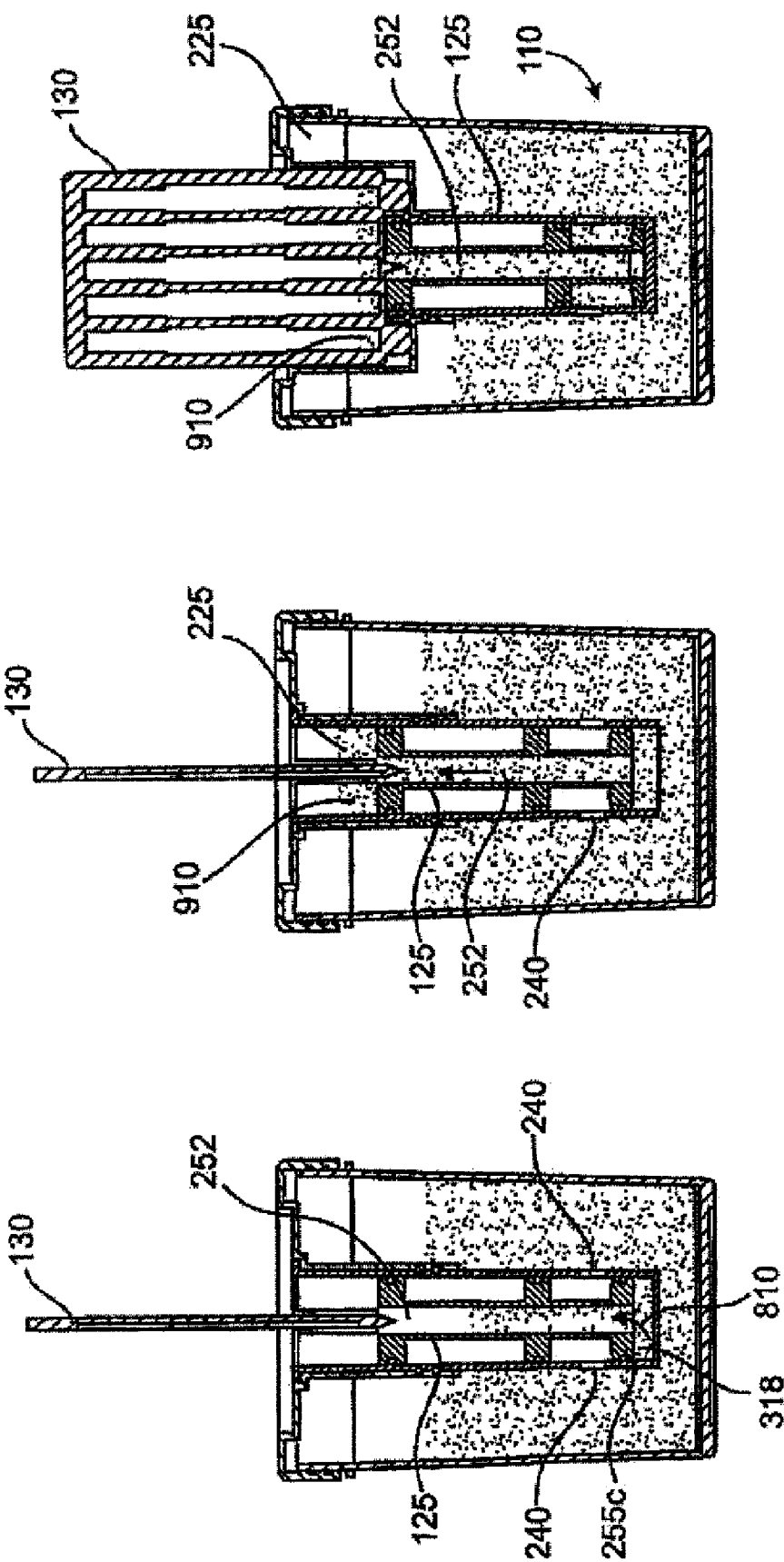

BIOLOGICAL SPECIMEN COLLECTION AND ANALYSIS SYSTEM

REFERENCE TO PRIORITY DOCUMENT

This application claims priority of U.S. Provisional Patent Application Ser. No. 60/497,853 entitled "Biological Specimen Collection and Analysis System", filed Aug. 25, 2003. Priority of the aforementioned filing date is hereby claimed, and the disclosure of the Provisional Patent Application is hereby incorporated by reference in its entirety.

BACKGROUND OF THE INVENTION

1. Field of the Invention

This invention relates generally to specimen collection devices and, more particularly, to a system that can be used to isolate and analyze a portion of a collected fluid specimen.

2. Description of the Related Art

It is often desirable to perform one or more tests on a bodily fluid specimen, such as to detect the presence of an illegal drug substance or a pregnancy indicator. The fluid specimen is commonly collected in a container, which is then closed and transported to a test center. A human operator then opens the container and exposes at least a portion of the fluid specimen to a test element, such as a test card, that can detect the presence or absence of a substance in the fluid specimen.

It is known that bodily fluid specimens can be infectious. Consequently, when the fluid specimen is being tested, it is desirable to isolate the portion of the specimen being tested from the human operator and from the general environment. One reason for this is to reduce the likelihood of the fluid specimen contaminating the general environment and to also reduce the likelihood of the human operator being contaminated. Another reason is to reduce the likelihood that the human operator or the general environment will contaminate the fluid specimen and introduce an inaccuracy in the testing of the fluid specimen.

In certain circumstances, it can also be desirable to conduct a test on just a portion of the fluid specimen and to leave the remaining, untested portion of the fluid specimen in an undisturbed state. In such cases, one primary concern is that the portion of the fluid specimen being tested does not contaminate the remaining, untested portion of the fluid specimen. Thus, it is desirable that the collection apparatus provide a means for segregating a portion of the fluid specimen so that the separated portion does not have any contact with the remainder of the fluid specimen.

In view of the foregoing, there is a need for a fluid specimen collection system that permits collection of a fluid specimen in a secure manner so as to reduce the risk of contamination and that also permits a portion of the fluid specimen to be segregated in an easy manner.

SUMMARY

Disclosed is a device for collecting a fluid specimen. The device comprises a container that can receive a fluid specimen; a plunger movably positioned within the container, wherein the plunger can move from an initial position at an upper region of the container to a secondary position below the first position; a fluid segregation chamber that can receive a portion of the fluid specimen from the container, wherein any fluid in the segregation chamber is segregated from the fluid specimen in the container; a fluid flow lumen that provides a passageway for at least a portion of the fluid specimen to flow into the fluid segregation chamber, wherein a first end of the passageway has a first opening that opens into the fluid segregation chamber and a second end of the passageway has a second opening that can receive at least a portion of the fluid specimen; and a seal member that covers the first opening or the second opening to prevent fluid from flowing therethrough. A test element can be used to push the plunger from the initial position toward the secondary position to break the seal member and cause at least a portion of the fluid specimen to flow through the second opening into the fluid flow lumen and into the fluid segregation chamber through the first opening.

Also disclosed is a method of analyzing a fluid specimen. The method comprises providing a container that contains the fluid specimen, the container including a fluid segregation chamber that can segregate at least a first portion of the fluid specimen from a second portion of the fluid specimen, wherein a fluid flow lumen provides a fluid passageway for a portion of the fluid specimen to flow from the container into the fluid segregation chamber, the fluid flow lumen having a seal that prevents fluid from flowing into the fluid flow lumen; and inserting a test element into the container so that the seal is punctured and the test element depresses a plunger to cause at least a portion of fluid in the container to flow into the fluid flow lumen and into the fluid segregation chamber, wherein at least a portion of the test element moves into the fluid segregation chamber in contact with the portion of the fluid specimen in the fluid segregation chamber.

Also disclosed is a device for collecting a fluid specimen. The device comprises a container that defines a main chamber that can receive a fluid specimen; a fluid segregation chamber coupled to the container for segregating at least a portion of the fluid specimen from the main chamber; a fluid flow lumen that provides a passageway for fluid to flow into the fluid segregation chamber from the main chamber, the fluid flow lumen having an upper opening that opens into the segregation chamber; a seal that covers the upper opening of the fluid flow lumen to prevent fluid from flowing through the upper opening; and a plunger coupled to the container, wherein the plunger can be moved in a downward direction to force at least a portion of the fluid specimen to flow into the fluid flow lumen toward the fluid segregation chamber, wherein the seal must be broken in order for the plunger to be moved in a downward direction.

Other features and advantages of the present invention should be apparent from the following description of various embodiments, which illustrate, by way of example, the principles of the invention.

BRIEF DESCRIPTION OF THE DRAWINGS

FIG. 5 is a cross-sectional view of the assembled specimen collection system, which is shown containing a biological specimen.

FIG. 6 is a cross-sectional view of the assembled specimen collection system containing a specimen and with a test card preparing to actuate the system.

FIG. 7 is another cross-sectional view of the assembled specimen collection system, the section view in FIG. 7 taken 90° from the section view of FIG. 6.

FIG. 8 is a cross-sectional view of the assembled specimen collection system with the test card actuating the system to cause a portion of the specimen to flow into a fluid segregation chamber.

FIG. 9 is a cross-sectional view of the assembled specimen collection system with the test card in a test position.

FIG. 10 is another cross-sectional view of the assembled specimen collection system with the test card in a test position as shown in FIG. 9, the section view in FIG. 10 taken 90° from the section view of FIG. 9.

DETAILED DESCRIPTION

Definitions

Unless defined otherwise, all technical and scientific terms used herein have the same meaning as commonly understood by one of ordinary skill in the art to which this invention belongs.

"Assaying" denotes testing for or detecting the presence of a substance or material, such as, but not limited to, a chemical, an organic compound, an inorganic compound, a metabolic product, a drug or a drug metabolite, an organism or a metabolite of such an organism, a nucleic acid, a protein, or a combination thereof. Optionally, assaying denotes measuring the amount of the substance or material. Assaying further denotes an immunological test, a chemical test, an enzymatic test, and the like.

"Sample" or "specimen" may be used interchangeably. "Sample" or "specimen" denotes any material to be assayed for the presence and/or concentration of an analyte in a sample or specimen, or to determine the presence and/or numbers of one or more components of a sample or specimen, or to make a qualitative assessment of a sample or specimen. A sample can be a fluid sample, such as a liquid sample. Examples of fluid samples that may be assayed include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

Specimen Collection and Analysis System

Figure 1:
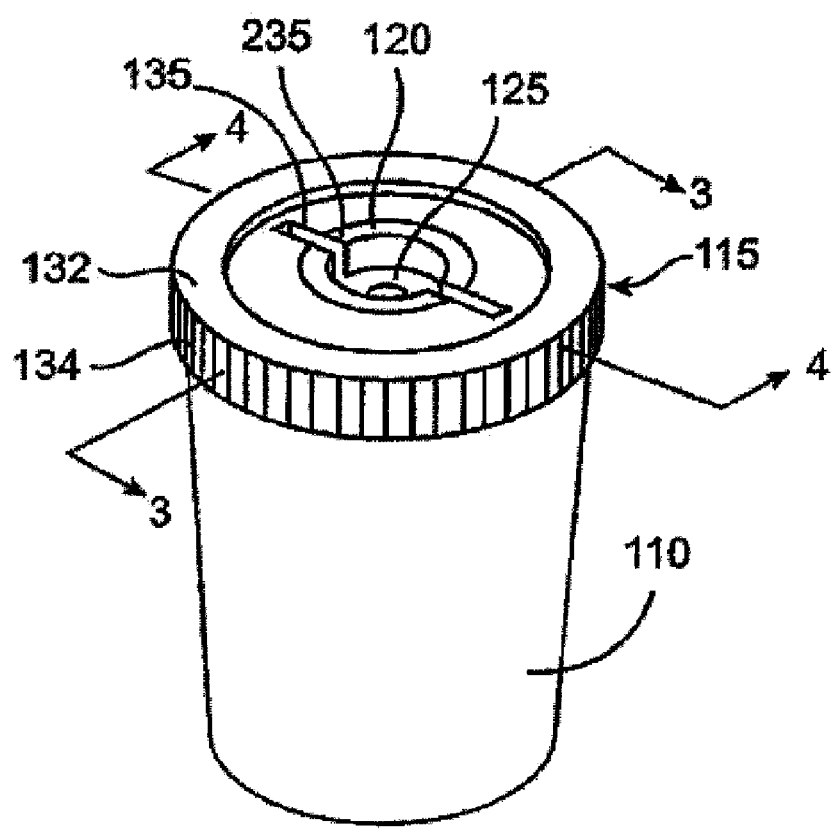
FIG. 1 is a perspective view of a specimen collection system of the present invention in an assembled state.
Figure 2:
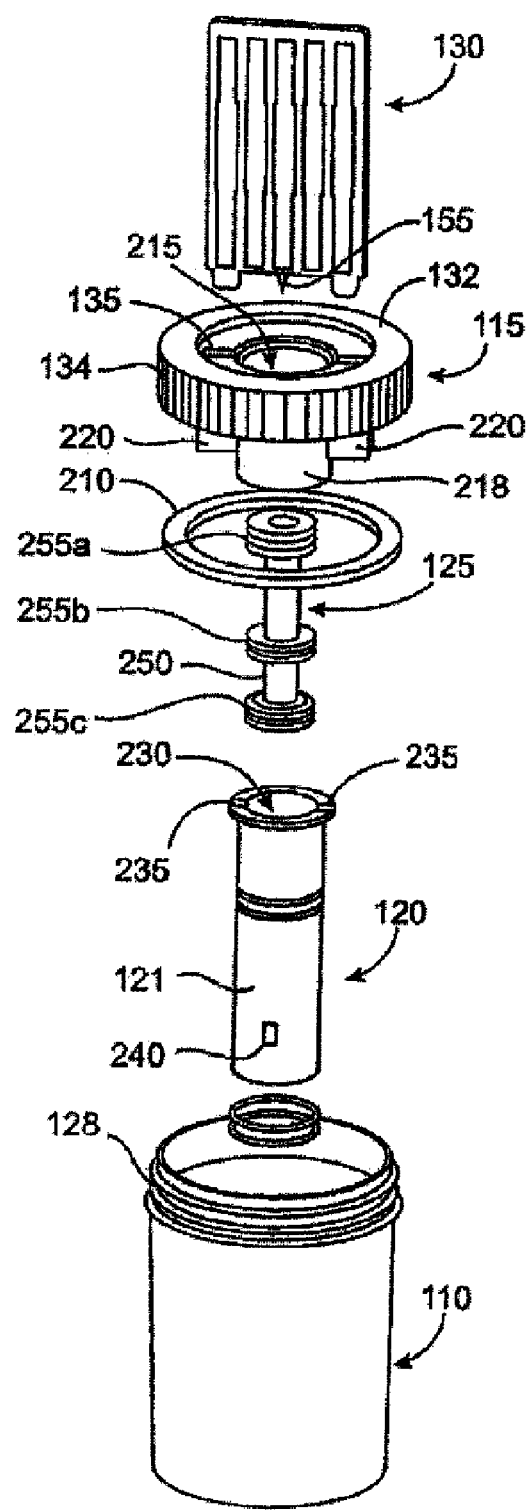
FIG. 2 is a perspective view of the specimen collection system in an exploded state.

FIG. 1 is a perspective view of a specimen collection system in an assembled state and FIG. 2 is a perspective view of the specimen collection system in an exploded state. The system includes a container 110, a cap 115, a plunger housing 120, a plunger 125, and a test element, such as a test card 130 (the test card 130 is shown in FIG. 2). The components of the system are described in detail below.

As described in detail below, the specimen collection system can be used to collect a fluid specimen in the container 110 and to segregate at least a portion of the specimen within a segregation chamber. The segregated portion is easily separated from the remainder of the fluid specimen by inserting a test element through the cap 115, which breaks a seal and pushes the plunger 125 downward into the container 110. This forces a portion of the fluid specimen to flow into the segregation chamber.

The test element is shown in the form of a test card 130, which can be any type of device that is configured to assay a specimen. The test card has a size and shape that is configured to be inserted into the container 110, as described in detail below. It should be appreciated that the size and shape of the test card 130 can vary.

With reference to FIGS. 1 and 2, the container 110 generally has a cup-like appearance and includes a base and at least one side wall that extends upwardly from the base so that the container 110 can contain a fluid specimen. An upper rim 128 (shown in FIG. 2) of the container 110 defines an opening that can receive fluid. In addition, the upper rim 128 of the container has threads that mate with corresponding threads on the cap 115 during coupling of the cap 115 to the container 110. Alternately, other types of mating configurations can be used to couple the cap 115 to the container 110, such as a press-fit configuration or a bayonet configuration.

With reference to FIG. 1, the cap 115 has a base 132 and a downwardly-extending flange 134, which has a shape that corresponds to the shape of the rim 128 of the container 110 so that the flange 134 can couple to the rim 128, such as by inserting the flange 134 over the rim 128. In the illustrated embodiment, the base 132 includes a circular depression that can be used as a seat for stacking another container 110 on top of the cap 115. It should be appreciated, however, that the base 132 can also be flat, as described below in other embodiments.

The inner surface of the flange 134 can have threads (not shown) that mate with the corresponding threads on the rim 128 of the container 110. In this manner, the cap 115 can be coupled to the container 110, such as by rotating the cap 115 on the container 110 so that the threads on the cap 115 couple with the corresponding threads on the rim 128 of the container 110. At least one sealing member, such as an o-ring 210 (shown in FIG. 2), can be positioned between the cap 115 and the container 110 to provide a seal therebetween.

With reference to FIGS. 1 and 2, a test card slot 135 extends through the base 132 of the cap 115. The test card slot 135 is sized to receive the test card 130, as described more fully below. The test card slot 135 generally has a size and shape that corresponds to the size and shape of the test card 130 in order to allow for a smooth fit of the test card 130 into the test card slot 135 during use. In the illustrated embodiment, the test card 130 has a flat, rectangular shape. Accordingly, the test card slot 135 has an oblong, rectangular shape that can receive the test card 130 therethrough. It should be appreciated that the test card slot 135 can have other shapes that correspond to differently-shaped test cards 130.

As best shown in FIG. 2, a shaft 215 is centrally-located on the cap 115 and is sized to receive at least a portion of the plunger housing 120. The shaft 215 is open at the top and bottom and is enclosed on the sides by a downwardly-extending housing 218 of the cap 115. The housing 218 comprises a set of walls that define a shape that corresponds to the outer shape of the plunger housing 120. In this manner, the shaft 215 can receive the plunger housing 120 when the system is assembled. In the illustrated embodiment, the plunger housing 120 and housing 218 are cylindrical, although they can have other shapes. The test card slot 135 also extends through the housing 218.

As shown in FIGS. 1 and 2, the shaft 215 is positioned to intersect the test card slot 135 so that a gap is centrally-positioned in the slot. A slot housing 220 (shown in FIG. 2) peripherally encloses the test card slot 135. The slot housing 220 extends downwardly from the cap base 132 and outwardly from the housing 218.

The slot housing 220 and an upper region of the plunger housing 120 collectively define an interior fluid segregation chamber 225 (shown in FIG. 4) that is described in more detail below. The test card slot 135 communicates with the fluid segregation chamber 225 and provides a passageway for introducing the test card 130 into the fluid segregation chamber 225. As described below, the fluid segregation chamber 225 receives at least a portion of the fluid specimen from the container 110 when the plunger 125 is actuated during use.

With reference to FIG. 2, the plunger housing 120 has an elongated, cylindrical shape. The plunger housing 120 has annular sidewall 121 that provides the plunger housing 120 with a cylindrical shape, although it can also have other shapes. An internal plunger shaft 230 extends vertically through the plunger housing 120. The plunger shaft 230 forms an opening in the upper end of the plunger housing 120, the opening being sized to receive the plunger 125. The plunger shaft 230 is enclosed at its bottom end by a bottom wall 122 (shown in FIG. 3) of the plunger housing 120. At least one fluid entry port 240 comprised of a hole or opening is located on the lower side region of the plunger housing 120.

A pair of opposed test card slots 235 extend through the top end of the plunger housing 120. The test card slots 235 align with the test card slot 135 on the cap 115 when the system is assembled. As shown in FIG. 1, the test card slot 135 in the cap 115 and the test card slots 235 in the plunger housing 120 collectively form a single slot that can receive the test card 130 therethrough.

With reference again to FIG. 2, the plunger 125 includes an elongate plunging arm 250. A fluid flow lumen 252 extends vertically through the plunging arm 250 such that the fluid flow lumen 252 forms openings through the top and bottom ends of the plunger arm 250. As described below, fluid can flow through the fluid flow lumen from the container 110 and into the fluid segregation chamber 225.

With reference still to FIG. 2, a plurality of guide members 255 are positioned in intervals along the length of the plunging arm 250 (the guide members are referred to collectively using the reference numeral 255 and individually using the reference numeral 255 followed by a letter suffix). The guide members 255 comprise protrusions that extend outwardly from the plunging arm 250. At least one of the guide member 255 has a shape and dimension that generally conforms to the cross-sectional shape and dimension of the internal plunger shaft 230 of the plunger housing 120. In this manner, the plunger 125 can be slidably positioned within the plunger shaft 230, with the guide member(s) 255 acting as guides that permit the plunger 125 to slide upwardly and downwardly in the plunger shaft 230 without substantial wobble. The guide members 255 can sealingly engage with the internal walls of the plunger shaft 230 so that the guide members 255 prevent fluid from flowing between the guide members 255 and the internal walls of the plunger shaft 230. In the illustrated embodiment, the plunger 125 includes an upper guide member 255a located at a top end of the plunging arm 250, a middle guide member 255b located at the middle of the plunging arm, 250, and a bottom guide member 255c located at a bottom end of the plunging arm 250. It should be appreciated that the plunger 125 can include more or less guide members 250 and that the guide members 250 can be positioned at various locations and intervals on the plunging arm 250.

Figure 4:
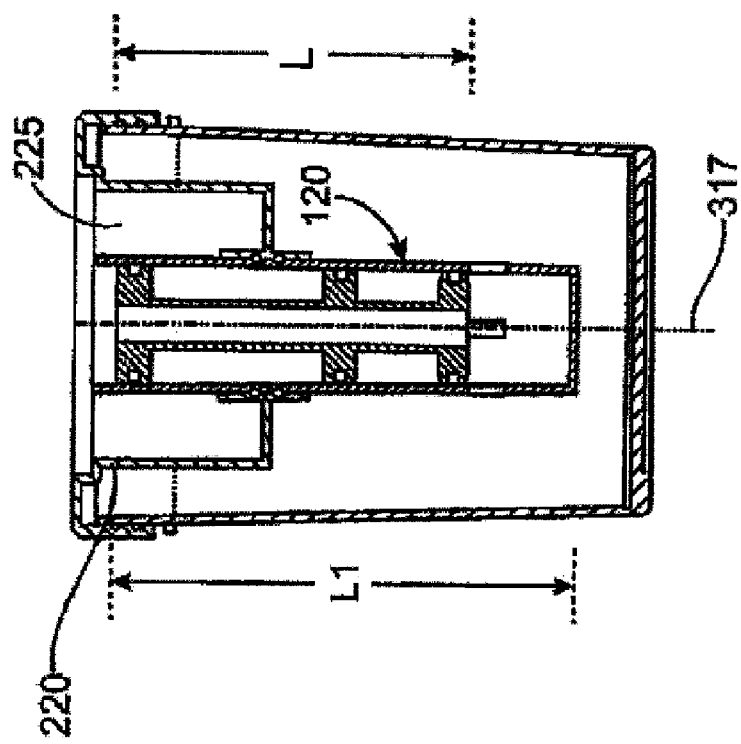
FIG. 4 is a cross-sectional view of the assembled specimen collection system along line 4-4 of FIG. 1.
Figure 3:
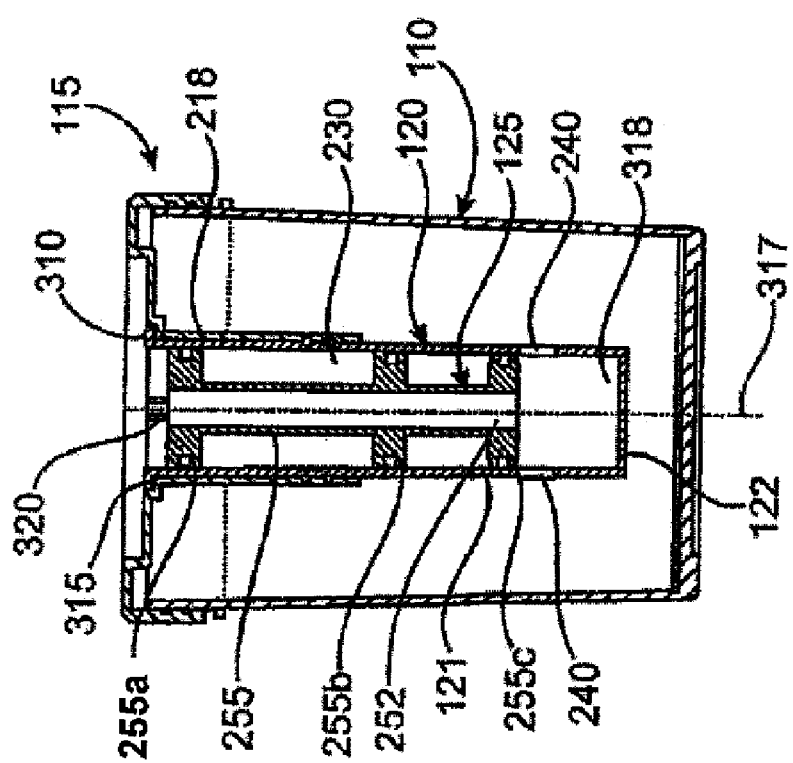
FIG. 3 is a cross-sectional view of the assembled specimen collection system along line 3-3 of FIG. 1.

The assembled specimen collection system is now described in more detail with reference to FIGS. 3 and 4. FIG. 3 is a cross-sectional view of the assembled system along line 3-3 of FIG. 1 and FIG. 4 is a cross-sectional view of the assembled system along line 4-4 of FIG. 1. With reference to FIG. 3, in the assembled state, the cap 115 is coupled to the top of the container 110. As mentioned, the cap 115 and container 110 both have threads that mate to allow the cap 115 to be screwed onto the container 110. One or more o-rings can be positioned between the cap 115 and container 110 for providing a seal. It should be appreciated that other mating means can be used to couple the cap 115 to the container 110.

With reference to FIG. 3, when the system is assembled, the plunger housing 120 is concentrically positioned within the housing 218 such that the housing 218 surrounds at least a portion of the plunger housing 120. The top end of the plunger housing 120 is supported by the cap 115 and the remainder of the plunger housing 120 extends downwardly into the container 110. In this regard, the top end of the plunger housing 120 has a lip 310 that is positioned within a correspondingly-shaped seat 315 in the cap 115 to provide a smooth fit between the cap 115 and the plunger housing 120. Alternately, the plunger housing 120 can be integrally formed with the cap 115, as described below in other embodiments. It should be appreciated that various components of the fluid collection system can be integrally formed as single or plural pieces according to design and manufacturing criteria.

In one embodiment, the plunger housing 120 is sized such that the fluid entry ports 240 are located in a bottom region of the container 110 when the plunger housing 120 is positioned in the shaft 215. This increases the likelihood that fluid specimen in the container 110 will flow into the entry ports 240. However, it should be appreciated that the location of the fluid entry ports 240 can vary.

With reference to FIG. 3, the plunger 125 is slidably positioned within the plunger shaft 230 of the plunger housing 120. As mentioned, the sizes and shapes of the guide members 255 correspond to the size and shape of the plunger shaft 230 in the plunger housing 120. In this manner, the plunger 125 can be slidably and securely positioned within the plunger shaft 230 with the peripheral edges of the guide members 255 abutting the internal walls of the plunger shaft 230. When positioned as such, the plunging arm 255 co-axially aligns with a vertical axis 317 of the plunger shaft 230.

As shown in FIG. 4, the plunger 125 has a length L that is shorter than the length L1 of the plunger shaft 230. Accordingly, the relative lengths provide additional space within the plunger shaft 230 so that the plunger 125 can slide in both an upward and downward direction within the plunger shaft 230 of the plunger housing 120.

In an initial state, which is shown in FIG. 3, the plunger 125 is positioned such that the top end of the plunger 125 is located at or near the top of the plunger housing 120. As mentioned, the plunger 125 has a length L that is smaller than the length L1 of the plunger shaft 230. The relative lengths of L and L1 are such that when the plunger 125 is in the initial state, the bottom end of the plunger 125 is located above the fluid entry ports 240 of the plunger housing 120. In addition, the relative lengths of L and L1 are such that a reservoir chamber 318 is formed within the lower end of the plunger shaft 230. The guide member 255c on the lower end of the plunger 120 defines the upper end of the reservoir chamber 318. The internal side wall(s) of the plunger housing 120 define the sides of the reservoir chamber 318, and the internal bottom wall 122 of the plunger housing 120 defines the lower end of the reservoir chamber 318.

The fluid flow lumen 252 forms a first opening in the upper end of the plunger 125, wherein the first opening opens into the fluid segregation chamber 225 when the plunger is moved downward, as described below. The fluid flow lumen 252 communicates with the reservoir chamber 318 via a second opening in the bottom end of the plunger 125. The second opening provides a passageway for fluid to flow into the fluid flow lumen 252 from the reservoir chamber 318. The plunger 125 can move in a downward direction through the reservoir chamber 318 during actuation of the plunger in order to cause fluid to flow into the fluid flow lumen 252, as described more fully below.

As shown in FIG. 3, a seal member 320 is located on the top of the plunger 125. The seal member 320 entirely covers the upper, open end of the fluid flow lumen 252 so as to prevent fluid from flowing out the fluid flow lumen into the segregation chamber 225. In one embodiment, the seal member 320 is a strip or band of adhesive material that is sized and shaped to entirely cover the upper opening in the fluid flow lumen 252. The seal member 320 is made of a material that can be punctured when a sufficient amount of pressure is applied to the seal member 320.

As discussed above, at least a portion of the cap 115 forms a fluid segregation chamber 225 that communicates with the test card slot 135. This is shown in more detail in FIG. 4. The fluid segregation chamber 225 is a chamber that is contained within the slot housing 220 and the plunger housing 120. As described below, at least a portion of the test card 130 can be inserted into the fluid segregation chamber 225 by inserting the test card 130 through the slot 135 in the cap 115 and the slot 235 in the plunger housing 120. Toward this end, a bottom portion of the test card 130 includes a structure that can break or puncture the seal member when the test card 130 is inserted through the slots. For example, in the embodiment shown in FIG. 2, the test card 130 includes a puncture device comprised of a sharp protrusion 155 that can be used to puncture the seal member 320.

The use of the specimen collection system is now described with reference to FIGS. 5-10. In an initial step, a fluid specimen is first collected in the container 110. This can be accomplished, for example, by providing the container 110 and the detached cap 115 to a subject that will provide the biological specimen. The subject then collects the fluid specimen in the container 110, such as, for example, by urinating into the container 110. It should be appreciated that specimen can be provided in other manners. The cap 115 is then coupled to the container, such as by screwing the cap 115 onto the container 110 or by using some other mechanism. The capped container 110 thus contains a fluid specimen 510, as shown in FIG. 5. The specimen 510 resides in a main chamber 512 of the container 110, wherein the main chamber 512 is separated from the segregation chamber 225 (shown in FIG. 7) of the container 110. At least a portion of the specimen 510 flows through the entry ports 240 into the reservoir chamber 318, as exhibited by the arrows labeled 514 in FIG. 5.

At this stage of the procedure, the specimen 510 in the reservoir chamber 318 will not flow into the fluid flow lumen 252, as the fluid flow lumen 252 contains air and is sealed or closed at the upper end by the seal member 320. In addition, the bottom guide member 255c forms a seal with the internal walls of the plunger housing 120 to prevent any fluid from flowing between the guide member 255c and the internal walls of the plunger housing 120. Thus, the bottom guide member 255c prevents the specimen from flowing upwardly through the plunger housing 120 past the bottom guide member 255c. Even if some fluid specimen should flow into the fluid flow lumen 252, the seal member 320 covers the upper end of the specimen 510 and prevents the specimen 510 from flowing into the segregation chamber 225.

With reference to FIGS. 6 and 7, the test card 130 is next inserted into the test card slot in the cap 115. The test card 130 is moved downward such that the protrusion 155 on the bottom end of the test card 130 breaks through the seal member 320, such as by puncturing a hole in the seal member 320. This broken seal 320 provides an opening between the upper end of the fluid flow lumen 252 and the segregation chamber 225. As best shown in FIG. 7, the bottom portion of the test card 130 now protrudes into the segregation chamber 225 through the test card slot. At this stage of the operation, the segregation chamber 225 is empty. That is, the segregation chamber does not contain any of the specimen 510.

As shown in FIG. 7, a bottom edge of the test card 130 abuts an upper edge of the plunger 125. More specifically, the bottom edge of the test card 130 abuts the upper guide member 255a, although the test card 130 can abut other portions of the plunger 125. When the test card 130 is positioned relative to the plunger 125 as such, the test card 130 can be used to push the plunger 125 in a downward direction through the plunger housing 120.

With reference to FIG. 8, a user next pushes the test card 130 in a downward direction. Because the test card 130 abuts the upper end of the plunger 125, the test card 130 pushes the plunger 125 in a downward direction as the test card 130 moves downward. The bottom guide member 255c of the plunger 125 thus travels downwardly through the reservoir chamber 318 and reduces the volume of the reservoir chamber 318. As it moves downward through the reservoir chamber, the bottom guide member 255c displaces the fluid in the reservoir chamber 318.

While this occurs, the bottom guide member 255c travels downward past the fluid entry ports 240, as shown in FIG. 8. As mentioned, the bottom guide member 255c has a sealing engagement with the internal wall of the plunger shaft 230 so that the guide member 255c blocks the specimen 510 from flowing into the fluid entry ports 240. Thus, the fluid specimen 510 in the reservoir chamber 318 is prevented from exiting the reservoir chamber 318 through the fluid entry ports 240. As the volume of the reservoir chamber 318 decreases due to the downward movement of the plunger 125, the fluid specimen 510 is forced to travel upward into the fluid flow lumen 252 through the hole in the bottom end of the plunger 125, as represented by the arrow 810 in FIG. 8. As mentioned, the seal member 320 was previously punctured, which opened the upper end of the fluid flow lumen 252, thereby allowing any air in the fluid flow lumen 252 to escape as the fluid specimen flows into the fluid flow lumen 252.

As shown in FIGS. 9 and 10, the portion 910 of the fluid specimen 510 that was in the reservoir chamber 318 continues to flow upward through the fluid flow lumen 252 as the plunger 125 moves downward. Eventually, the portion 910 of the fluid specimen 510 flows into the segregation chamber 225 through the upper, open end of the fluid flow lumen 252. Thus, the portion 910 of the fluid specimen 510 fills at least a portion of the segregation chamber 225, as shown in FIGS. 9 and 10. While the foregoing has occurred, the test card 130 has moved downward so that at least a portion of the test card 130 is also positioned within the segregation chamber 225. In this manner, the test card 130 is exposed to the fluid specimen contained in the segregation chamber 225.

Figure 11:
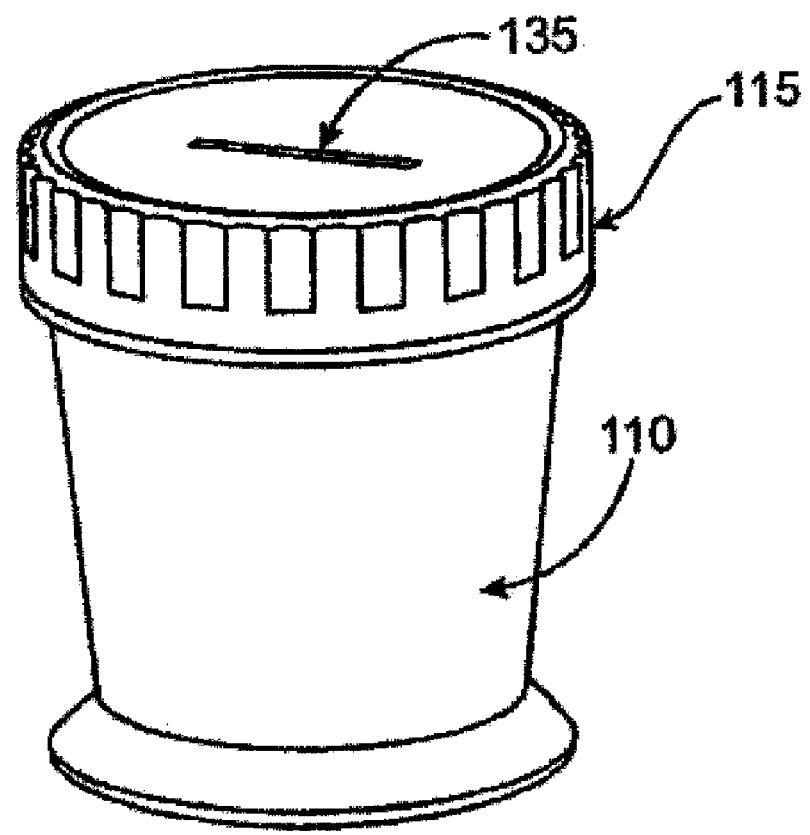
FIG. 11 is a perspective view of a second embodiment of the specimen collection system.
Figure 12:
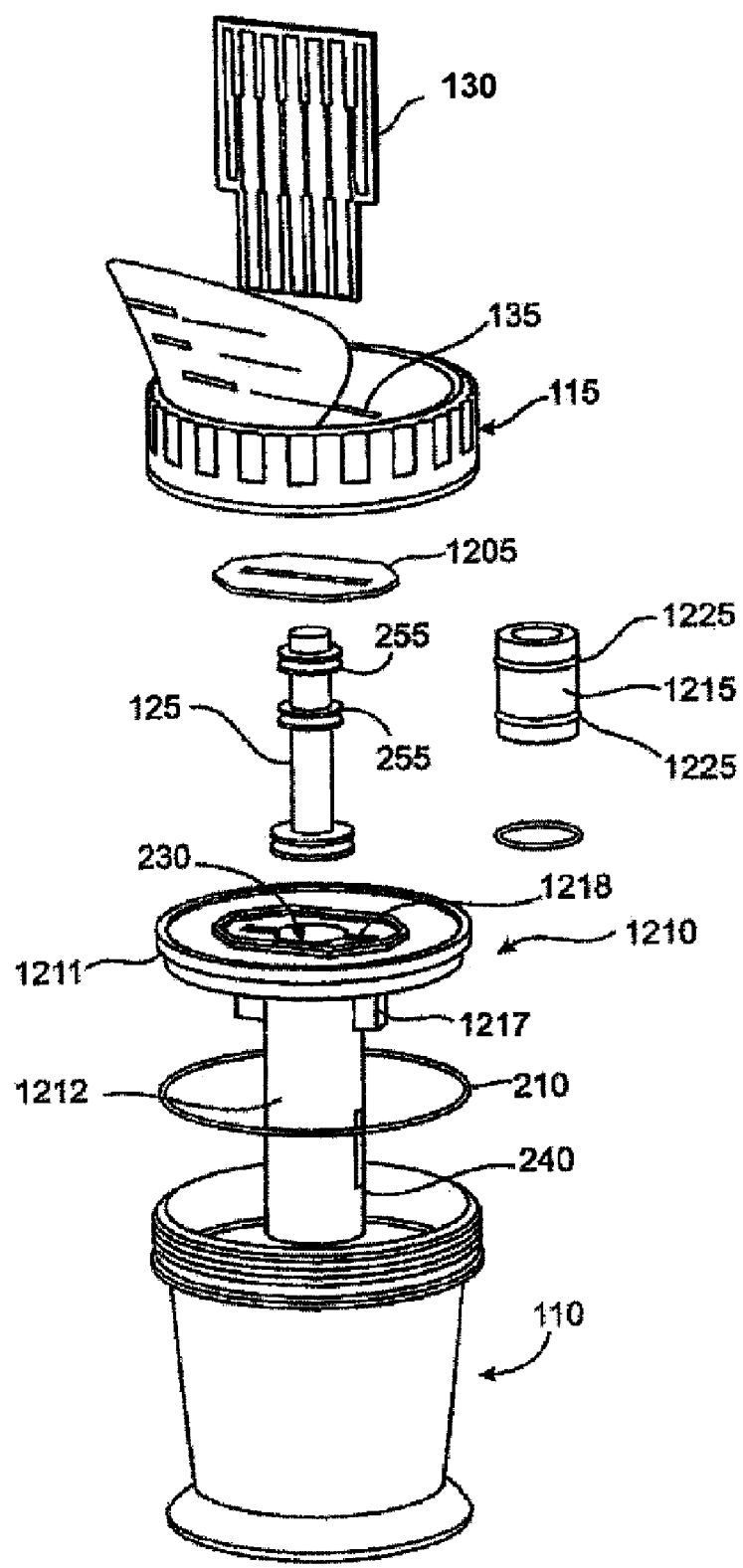
FIG. 12 is an exploded view of the specimen collection system of FIG. 11.

There is now described a second embodiment of the specimen collection system. Unless otherwise noted, like numerals refer to like parts. With reference to FIGS. 11 and 12, the second embodiment includes the container 110 and the cap 135. The slot 135 is located directly in the cap 115.

As best shown in FIG. 12, a seal 1210 can be removably positioned on the cap 115 so as to sealingly cover the slot 135. The seal 1210 can be manufactured of a flexible material. A bottom gasket 1205 is located on the cap directly below the slot 135.

With reference still to FIG. 12, a plunger housing 1210 includes a cap interface 1211 that has a shape that can engage the bottom of the cap 115. In the illustrated embodiment, the cap interface 1211 has a circular, disk-like shape that conforms to the shape of the bottom of the cap 115 to allow the cap interface to smoothly engage the cap 115. It should be appreciated that the cap interface 1211 can have other shapes.

The plunger housing 1210 further includes a chamber housing 1217 that at least partially or entirely encloses the internal segregation chamber 225 into which the test card 130 can be inserted via the slot 135. In this regard, a corresponding slot 1218 is located in the cap interface 1211 for receiving test card 130.

The plunger housing 1210 also includes cylindrical portion 1212 that extends downwardly from the cap interface 1211. The cylindrical portion 1212 defines the internal plunger shaft 230 in which the plunger 125 can movably slide, as described in the previous embodiment. At least one fluid entry port 240 is located on the cylindrical portion 1212 to provide fluid access to the plunger shaft 230.

With reference still to FIG. 12, a cylindrical guide 1215 is dimensioned to be slidably positioned within the plunger shaft 230. The cylindrical guide 1215 has an internal lumen that slidably receives an upper region of the plunger 125. The cylindrical guide 1215 includes one or more detents, such as circular ridges 1225, that engage corresponding guide members 255 on the plunger 125 for securing position of the plunger 125 in the guide 1215.

Figure 13:
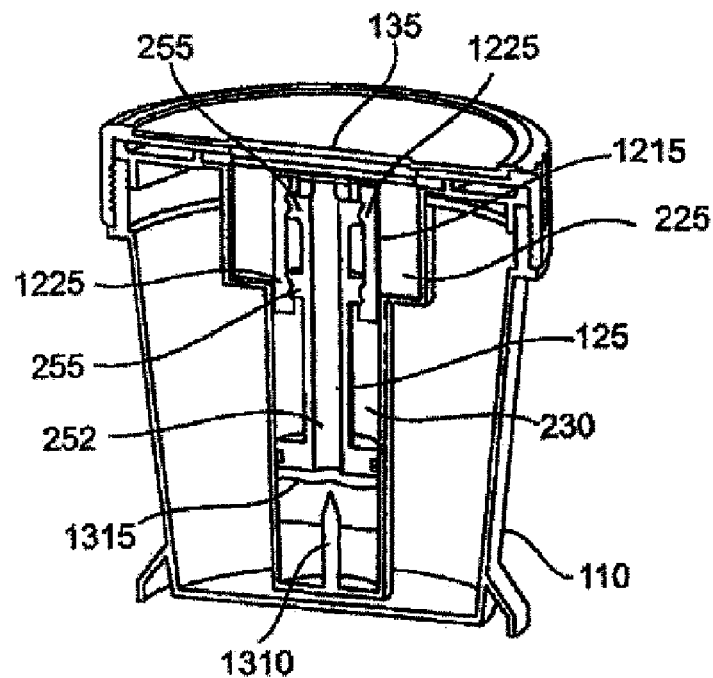
FIG. 13 is a cross-sectional view of the specimen collection system of FIG. 11.

FIG. 13 shows a cross-sectional, perspective view of the specimen collection system in an assembled state, with the plunger 125 in an initial position. The guide members 255 are engaged with the ridges 1225 to retain the plunger 125 in the initial position, which is elevated above a puncture device comprised of a sharp-edged protrusion 1310 that extends upwardly from the bottom of the container 110. A seal member 1315 is positioned on the bottom end of the plunger 125 so as to sealingly cover the hole formed by the bottom end of the fluid flow lumen 252 that extends through the plunger 125.

Figure 14:
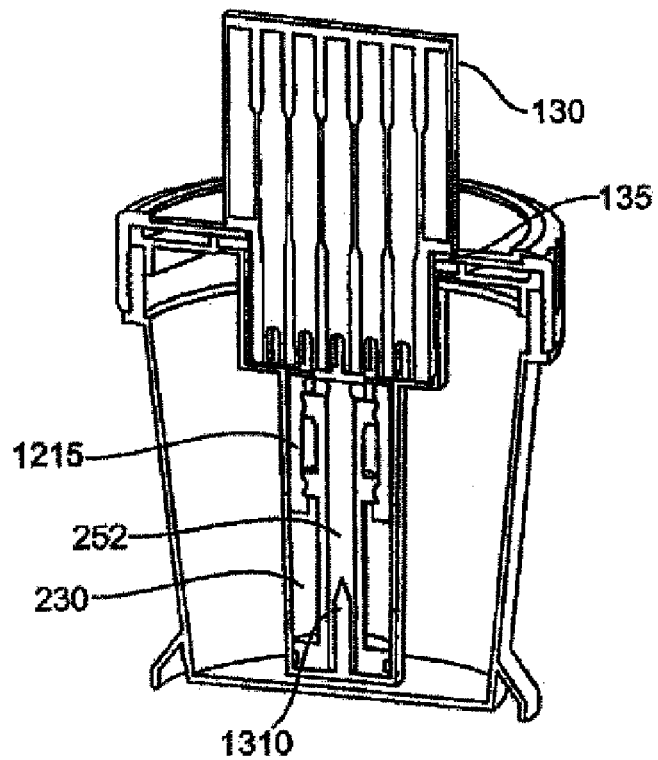
FIG. 14 is a cross-sectional view of the specimen collection system of FIG. 11.

As shown in FIG. 14, the plunger 125 can be forced into a secondary position wherein the plunger 125 has been moved downward such that the protrusion 1310 punctured the seal member 1315. The plunger 125 is moved to the secondary position by inserting the test card 130 into the slot 135 and pushing the test card 130 downward. This causes the bottom end of the test card 130 to abut the upper end of the plunger 125, thereby sliding the plunger 125 and the guide 1215 downwardly through the plunger shaft 230. The protrusion 1310 is now positioned within the fluid flow lumen 252. It should be appreciated that the protrusion 1310 can take on other forms and structures that are configured to puncture the seal member 1315 when the plunger 125 is moved downward.

Figure 17:
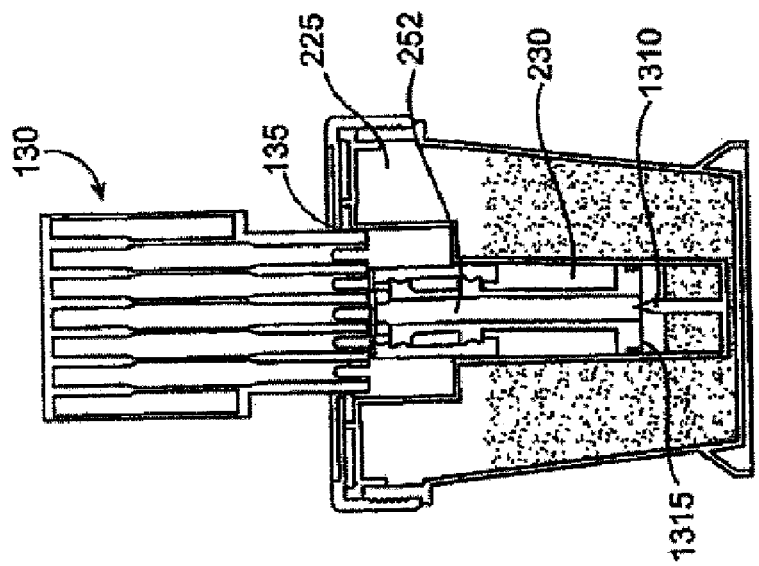
FIGS. 15-17 show various steps involved with using the specimen collection system.
Figure 16:
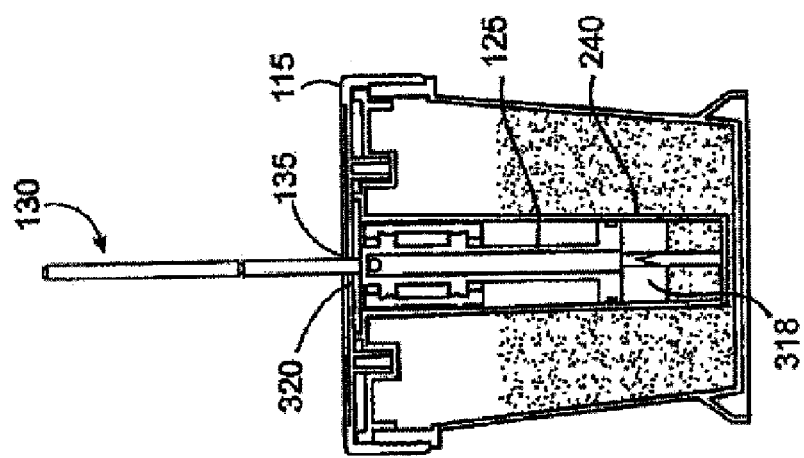
Figure 15:
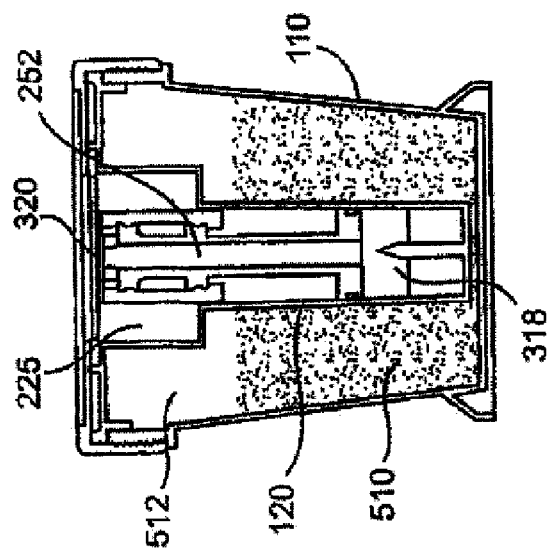

With reference to FIGS. 15-17, the operation of the specimen collection system is now further described. As shown in FIG. 15, the specimen 510 resides in a main chamber 512 of the container 110, wherein the main chamber 512 is separated from the segregation chamber 225 (shown in FIG. 7) of the container 110. The upper end of the fluid flow lumen 252 can be covered by a seal member 320 and the lower end can also be covered by a seal member (as was shown in FIG. 13).

As shown in FIG. 16, at least a portion of the specimen 510 flows through the entry ports 240 into the reservoir chamber 318. The test card 130 is inserted into the slot 135 in the cap 115 such that the lower end of the test card abuts the upper end of the plunger 125. With reference to FIG. 17, a user then pushes the test card 130 downward through the slot 135, which forces the plunger downwardly through the plunger shaft 230 The test card 130 can puncture the seal member 320 on the top end of the plunger 125. Alternatively, or in concert with the puncturing of the seal member 320, the protrusion 1310 can puncture the lower seal member 1315, if present, as the plunger 125 moves downward. The openings into the fluid flow lumen 252 are thereby unsealed so that the specimen in the reservoir chamber 318 can flow upwardly into the fluid flow lumen 252 and into the segregation chamber 225. As described above with respect to the previous embodiment, the test card 130 has moved downward so that at least a portion of the test card 130 is also positioned within the segregation chamber 225. In this manner, the test card 130 is exposed to the fluid specimen contained in the segregation chamber 225.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. A device for collecting a fluid specimen, comprising:
a container configured to receive the fluid specimen;
a plunger movably positioned within the container, wherein the plunger moves from a first position at an upper region of the container to a second position below the first position;
a fluid segregation chamber configured to receive a portion of the fluid specimen from the container, wherein fluid in the segregation chamber is segregated from fluid in the container;
a fluid flow lumen that provides a passageway for at least a portion of the fluid specimen to flow into the fluid segregation chamber, wherein a first end of the passageway has a first opening that opens into the fluid segregation chamber and a second end of the passageway has a second opening configured to receive at least a portion of the fluid specimen; and
a seal member that covers the first opening or the second opening, wherein the seal member prevents fluid from entering the fluid segregation chamber until the seal member is broken;
wherein the plunger is configured to move from the first position toward the second position upon insertion of a test element to effect breaking of the seal member and further causing at least a portion of the fluid specimen to flow through the second opening into the fluid flow lumen and out of the first opening into the fluid segregation chamber; and a slot extending through a cap and communicating with the fluid segregation chamber.

2. The device of claim 1, wherein the cap is coupled to the container, and a plunger housing that extends downwardly from the cap into the container, wherein the plunger housing comprises sidewalls and a bottom wall.

3. The device of claim 2, further comprising a reservoir chamber positioned in a lower region of the plunger housing, and wherein at least one fluid entry port is located in the side wall of the plunger housing so as to communicate with the reservoir chamber, the fluid entry port providing a pathway through which at least a portion of the fluid specimen flows into the reservoir chamber from the container.

4. The device of claim 3, wherein the second opening of the fluid flow lumen opens into the reservoir chamber, and wherein at least a portion of the plunger blocks fluid from flowing into the fluid entry port when the plunger moves from the first position toward the second position such that fluid in the reservoir chamber flows into the fluid flow lumen as the plunger moves toward the second position.

5. A device for collecting a fluid specimen, comprising:
a container configured to receive the fluid specimen;
a plunger movably positioned within the container, wherein the plunger moves from a first position at an upper region of the container to a second position below the first position;
a fluid segregation chamber configured to receive a portion of the fluid specimen from the container, wherein fluid in the segregation chamber is segregated from fluid in the container;
a fluid flow lumen that provides a passageway for at least a portion of the fluid specimen to flow into the fluid segregation chamber, wherein a first end of the passageway has a first opening that opens into the fluid segregation chamber and a second end of the passageway has a second opening configured to receive at least a portion of the fluid specimen;
wherein the fluid flow lumen is located within the plunger; and
a seal member that covers the first opening or the second opening, wherein the seal member prevents fluid from entering the fluid segregation chamber until the seal member is broken;
wherein the plunger is configured to move from the first position toward the second position upon insertion of a test element to effect breaking of the seal member and further causing at least a portion of the fluid specimen to flow through the second opening into the fluid flow lumen and out of the first opening into the fluid segregation chamber.

6. A device for collecting a fluid specimen, comprising:
a container configured to receive the fluid specimen;
a plunger movably positioned within the container, wherein the plunger moves from a first position at an upper region of the container to a second position below the first position;
a fluid segregation chamber configured to receive a portion of the fluid specimen from the container, wherein fluid in the segregation chamber is segregated from fluid in the container;
a fluid flow lumen that provides a passageway for at least a portion of the fluid specimen to flow into the fluid segregation chamber, wherein a first end of the passageway has a first opening that opens into the fluid segregation chamber and a second end of the passageway has a second opening configured to receive at least a portion of the fluid specimen;
a seal member that covers the first opening or the second opening, wherein the seal member prevents fluid from entering the fluid segregation chamber until the seal member is broken;
wherein the plunger is configured to move from the first position toward the second position upon insertion of a test element to effect breaking of the seal member and further causing at least a portion of the fluid specimen to flow though the second opening into the fluid flow lumen and out of the first opening into the fluid segregation chamber;
a cap that couples to the container; and
a plunger housing that extends downwardly from the cap into the container, wherein the plunger housing comprises sidewalls and a bottom wall;
wherein the plunger housing is removably attached to the cap.

7. A method of analyzing a fluid specimen, comprising:
providing the device of claim 1; and
inserting the test element into the container so that the seal is punctured and the test element depresses a plunger to cause at least a portion of fluid in the container to flow into the fluid flow lumen and into the fluid segregation chamber, wherein at least a portion of the test element moves into the fluid segregation chamber in contact with the portion of the fluid specimen in the fluid segregation chamber.

8. The method of claim 7, wherein the cap is coupled to a plunger housing that defines a plunger shaft in which the plunger is movably positioned.

9. The method of claim 8, wherein at least a portion of the fluid specimen flows into a reservoir chamber in a bottom region of the plunger housing when the cap is coupled to the container, and wherein the plunger decreases the volume of the reservoir chamber as the plunger is depressed to thereby force the portion of the fluid specimen in the reservoir chamber to flow into the fluid flow lumen.

10. The method of claim 9, wherein the portion of the fluid specimen flows into the reservoir chamber through at least one fluid entry port in the plunger housing, and wherein the plunger blocks the portion of the fluid specimen from flowing out of the reservoir chamber through the fluid entry port as the plunger is depressed.

11. The method of claim 7, wherein inserting the test element into the container comprises inserting the test element through the slot in the cap.

12. A device for collecting a fluid specimen, comprising:
a container comprising a main chamber that is configured to receive the fluid specimen;
a fluid segregation chamber coupled to the container for segregating at least a portion of the fluid specimen from the main chamber;
a fluid flow lumen that provides a passageway for fluid to flow from the main chamber into the fluid segregation chamber, the fluid flow lumen comprising an upper opening that provides access to the segregation chamber;
wherein the fluid flow lumen is positioned inside the plunger;
a seal member configured to cover the upper opening of the fluid flow lumen to prevent fluid from flowing through the upper opening to the segregation chamber; and
a plunger coupled to the container, wherein the plunger is configured to move in a downward direction to force at least a portion of the fluid specimen to flow into the fluid flow lumen toward the fluid segregation chamber, wherein the seal member prevents fluid from moving into the fluid segregation chamber until the seal is broken.

13. The device of claim 12, further comprising a cap coupled to the container, wherein the cap includes a plunger housing that extends downwardly into the container when the cap is coupled to the container.

14. The device of claim 13, wherein a lower region of the plunger housing forms a reservoir chamber, and wherein the fluid specimen in the main chamber flows into the reservoir chamber through a fluid entry port in the plunger housing when the cap is coupled to the container.

15. The device of claim 14, wherein the fluid flow lumen has a lower opening that opens into the reservoir chamber and wherein the plunger blocks fluid in the reservoir chamber from flowing through the fluid entry port as the plunger moves downward, and wherein, as the plunger moves downward, the plunger displaces the fluid specimen in the reservoir chamber to cause the fluid in the reservoir chamber to flow into the fluid flow lumen toward the segregation chamber.

16. The device of claim 12, wherein the container is configured to receive a test element.

17. The device of claim 1 wherein the slot is configured to be sized to receive the test element such that at least a portion of the test element is located in the fluid segregation chamber as the test element pushes the plunger from the first position toward the second position.

18. The device of claim 2 further comprising a plunger shaft located within the plunger housing.

19. The device of claim 13, wherein the plunger housing further comprises a shaft, wherein the plunger is configured to be translated through the shaft.

20. The device of claim 1, further comprising the test element, wherein the test element is configured to move the plunger from the first position toward the second position.

21. A method of analyzing a fluid specimen, comprising:
providing the device of claim 5; and
inserting the test element into the container so that the seal is punctured and the test element depresses a plunger to cause at least a portion of fluid in the container to flow into the fluid flow lumen and into the fluid segregation chamber, wherein at least a portion of the test element moves into the fluid segregation chamber in contact with the portion of the fluid specimen in the fluid segregation chamber.

22. The method of claim 21, wherein the device further comprises a cap coupled to a plunger housing that defines a plunger shaft in which the plunger is movably positioned.

23. The method of claim 22, wherein at least a portion of the fluid specimen flows into a reservoir chamber in a bottom region of the plunger housing when the cap is coupled to the container, and wherein the plunger decreases the volume of the reservoir chamber as the plunger is depressed to thereby force the portion of the fluid specimen in the reservoir chamber to flow into the fluid flow lumen.

24. The method of claim 23, wherein the portion of the fluid specimen flows into the reservoir chamber through at least one fluid entry port in the plunger housing, and wherein the plunger blocks the portion of the fluid specimen from flowing out of the reservoir chamber through the fluid entry port as the plunger is depressed.

25. The method of claim 21, wherein inserting the test element into the container comprises inserting the test element through a slot in the cap.

* * * * *